(12) United States Patent
Shinitzky et al.

(10) Patent No.: US 7,098,304 B1
(45) Date of Patent: Aug. 29, 2006

(54) ASSAY FOR THE DIAGNOSIS OF SCHIZOPHRENIA BASED ON A NEW PEPTIDE

(75) Inventors: Meir Shinitzky, Kfar Shmaryahu (IL); Michael Deckmann, Guebwiller (FR)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/647,457

(22) PCT Filed: Mar. 30, 1999

(86) PCT No.: PCT/IL99/00190

§ 371 (c)(1),
(2), (4) Date: Nov. 29, 2000

(87) PCT Pub. No.: WO99/51725

PCT Pub. Date: Oct. 14, 1999

(30) Foreign Application Priority Data

Apr. 2, 1998  (IL)  ..................... 123925

(51) Int. Cl.
*A61K 38/04*  (2006.01)
*C07K 5/00*  (2006.01)
(52) U.S. Cl. ..................... 530/326; 530/300
(58) Field of Classification Search ................ 530/300, 530/350, 387.1; 435/7.1, 7.92; 436/500
See application file for complete search history.

(56) References Cited

U.S. PATENT DOCUMENTS 6,008,001 A * 12/1999 Shinitzky .................... 435/7.2

FOREIGN PATENT DOCUMENTS

WO  94/26107  11/1994
WO  95/23970  9/1995

OTHER PUBLICATIONS

Russell et al., Biochem. J., 236:115-126, 1986.*
Immunogenicity and Antigenic Specificity in Basic and Clinical Immunology, Ed. By Stites and Terr, Appleton Lange, Norwalk, Conn., 1991, pp. 101-108.*
Skolnick et al., Trends in Biotech., 18(1):34-39, 2000.*
Jobling et al, Mol. Microbiol., 1991, 5(7):1755-67.*
Hedges etal., PNAS 91:2621-24, 1994 with alignment to SEQ ID No. 1.*
Hedges et al., PNAS 91:2621-24, 1994 with alignment Accession ID I50026 database PIR_78.*
Byrjalsen et al., WO98/10291, Mar. 12, 1998.*
Taylor et al., Experimental and Molecular Pathology, (Apr. 1985) 42(2)271-7.*
McAleese et al., Eur. J. Biochem., 178:413-17, 1988.*
Jankovic B D, Journal of Immunology (Aug. 1985) 135 (2 Suppl) 853s-857s.*
Blennow, K. et al., "Neuron specific enolase in cerebrospinal fluid: a biochemical marker for neuronal degeneration in demential disorders?" XP-002083586 *J Neural Transm* (P-D Sect) (1994) 8:183-191.
Gabriel, S. et al., "Increased Concentrations of Presynaptic Proteins on the Cingulate Cortex of Subjects With Schizophrinia" XP-002116909 *Arch Gen Psychiatry* vol. 54, (Jun. 1997) 559-566.
Ishiguro, A. et al "indentification of *Candida albincans* Antigens Reactive with Immunoglobulin Antibody of Human Sera" XP-002116908 *Infection and Immunity* (Apr. 1992) p. 1550-1557.
McAleese, Sybil M., et al., "Complete amino acid sequence of the neurone-specific γ isozyme of enolase (NSE) from human brain and comparison with the non-neuronal α form (NNE)". Eur. J. Biochem, 178, 413-417 (1988).
Oliva, Daniele, et al., "Complete Structure of the Human Gene Encoding Neuron-Specific Enolase". Genomics, 10, 157-165 (1991).
Egan, Michael F., et al., "Cereborspinal Fluid and Serum Levels of Neuron-Specific Enolase in Patients With Schizophrenia". Psychiatry Research, 43, 187-195 (1992).
D2: Database EBI, accession No. P06733 (sequence update: Jan. 4, 1988).

* cited by examiner

*Primary Examiner*—Sharon Turner
(74) *Attorney, Agent, or Firm*—Nath & Associates PLLC; Gary M. Nath; Susanne M. Hopkins

(57) ABSTRACT

The invention concerns peptides which bind antibodies that are found in elevated levels in body fluids of schizophrenic patients and are found at a lower level or not found at all in body fluids of non-schizophrenic individuals. Using a computerized program, the antigenic epitope of the peptides of the invention is predicted as having a core of hydrophobic amino acids which is surrounded by positively charged amino acids. The peptides of the invention are useful in the diagnosis of schizophrenia in an individual.

2 Claims, 4 Drawing Sheets

ASSAY FOR THE DIAGNOSIS OF SCHIZOPHRENIA BASED ON A NEW PEPTIDE

FIELD OF THE INVENTION

The present invention is generally in the field of assays for the diagnosis of mental disorders. More specifically, the present invention provides an assay for the diagnosis of schizophrenia.

PRIOR ART

The following is a list of prior art publications referred to in the present specification.
1. Carpenter, W. T., and Buchanan, R. W., Review, *N. Engl. J. Med,* 330681–690, 1994.
2. Knight, J. G., *Find. Exp. Clin. Pharmacol.,* 6:395408, 1984.
3. De Lisi, L. E., and Crow, T. J., *Psychiatr. Clin. North Am.,* 9:115–132, 1987.
4. Ganguli, R., Rabin, B. S., Kelly, R. H., Lyte, M. and Ragu, U., *Ann. N.Y. Acad. Sci.,* 496:676–690, 1987.
5. Shinitzky, M., Deckmann, M., Kessler, A., Sirota, P., Rabbs, A. and Elizur, A., *An. NY. Acad. Sci.,* 621:205–217, 1991.
6. Deckmann, M., Shinitzky, M., Leykin, I., Cheng, D., Guy, J., Avnon, M., Salganik, I., Amiri, Z., Schlossberg, A., Leibu, E., and Rafael, C., *The Italian J Psychiatr. Behav. Sci.,* 6:29–34, 1996.
7. PCT Patent Application Publication Number WO 95/23970.

The acknowledgement herein of the above art should not be construed as an indication that this art is in any way relevant to the patentability of the invention as defined in the appended claims.

The above publications will be acknowledged in the following by indicating their number from the above list.

BACKGROUND OF THE INVENTION

Schizophrenia is a syndrome which encompasses a variety of mental symptoms like auditory hallucinations, paranoia, delusions, catatonia, bizarre behavior or emotional withdrawal. Schizophrenia affects about 1% of the total population and its economical as well as social burden on society are enormous. The onset of the disease occurs at an early age and thus patients typically need life-long medical and psychiatric supervision. Schizophrenia is, therefore, rated as one of the most costly diseases in the industrial world[1].

There are various known risk factors associated with schizophrenia such as genetic predisposition, birth during winter and complications during pregnancy and birth. Viral infections and subsequent autoimmune reactions have also been proposed as possible causative factors[2-4]. The involvement of autoantibodies against platelets in schizophrenic patients was also shown as elevated levels of autoantibodies were detected in schizophrenic and demented patients as compared to control subjects, bipolar, depressed, personality disordered or schizoeffective patients[5-6]. Western Blot analysis revealed a pattern of platelet antigens recognized by autoantibodies obtained from schizophrenic patients which differed from that recognized by autoantibodies obtained from patients suffering from autoimmune thrombocytopenia and dementia[7]. The antigen bound specifically by autoantibodies obtained from schizophrenic patients has been characterized by its molecular weight.

SUMMARY OF THE INVENTION

In accordance with the invention, several proteins which bind autoantibodies that are found in elevated levels in body fluids of schizophrenic patients have been identified. The antibodies which these proteins bind are typically platelet associated autoantibodies (PAA). Such autoantibodies obtained from schizophrenic patients (hereinafter "schizophrenic derived antibodies—SDA") were shown to bind the above antigens while autoantibodies obtained from control non-schizophrenic individuals (hereinafter "non-schizophrenic derived antibodies—NSDA") did not.

The proteins which were shown to be capable of binding SDA were identified and further characterized by chemical and enzymatic methods. Some of the identified immunoreactive proteins are known proteins such as glyceraldehyde-3-phosphate dehydrogenase (G3PD), enolase, keratin, hepatocyte growth factor, extracellular calcium sensing receptor and several more. By digesting the rabbit protein enolase, an immunologically active peptide was revealed which had a high binding activity to SDAs.

The revealed peptide, being the immunologically active epitope of the enolase protein, comprised twenty eight amino acids of the following sequence:

SGETEDTFIADLVVGLCTGQIKTGAPCR (SEQ ID NO: 2)

On the basis of the revealed peptide, additional peptides were synthesized and highly active ones (i.e. such which had a high binding activity to SDAs as compared to a very low binding activity to NSDA or which do not bind NSDA at all) were identified. Moreover, the synthesized active peptides were capable of differentiating for the first time between plasma samples obtained from schizophrenic patients and plasma samples obtained from control non-schizophrenic individuals.

Further analysis of one of the synthesized highly active peptides (SEQ ID NO: 3) showed that this peptide forms a ring via two cysteins and a dimer via the remaining free cystein. The peptide in this form is most active in its ability to bind SDA.

As described below, the antigenic epitope of the synthetic highly active peptides of the invention seems to be a three dimensional spatial eptiope.

The present invention thus provides a peptide which binds antibodies that are found in elevated levels in body fluids of schizophrenic patients.

The invention further provides a peptide capable of binding antibodies that are found in elevated levels in body fluids of schizophrenic patients, wherein the peptide binds antibodies that are capable of specific binding to a peptide having the following amino acid sequence:

LVVGLCTCQIKTGPAC (SEQ ID NO: 3)

Several non-limiting examples of such peptides are the following:
iii. IADLVVGLCTGQIKTGAPCR (SEQ ID NO: 4)
iv. ADLVVGLCTGQIKTGAPCR (SEQ ID NO: 5)
v. DLVVGLCTGQIKTGAPCR (SEQ ID NO: 6)
vi. LVVGLCTGQIKTGAPCR (SEQ ID NO: 7)
vii. LVVGLCTGQIKTGPACR (SEQ ID NO: 8)
viii. LVVGLCTPQIKTGPACR (SEQ ID NO: 9)

The invention also provides a peptide which is capable of binding antibodies that are found in elevated levels in body fluids of schizophrenic patients, such peptides capable of binding antibodies which do not bind to peptides selected from the group consisting of:
i. SGETEDTFIADLVVGLCTGQ (SEQ ID NO: 10)
ii. VVGLCTGQIKTGAPCR (SEQ ID NO: 11)
iii. CTGQIKTGAPCR (SEQ ID NO: 12)
iv. LVVGLCTGQIKTGAPC (SEQ ID NO: 13)
v. LVVGLCTGQIKTGAP (SEQ ID NO: 14)
vi. LVVGLCTGQIKTGPAC (SEQ ID NO: 15)

The invention also provides a peptide capable of binding to antibodies that are found in elevated levels in body fluids of schizophrenic patients comprising an amino acid sequence selected from the group, consisting of:
i. SGETEDTFIADLVVGLCTGQIKTGAPCR (SEQ ID NO: 2)
ii. LVVGLCTCQIKTGPAC (SEQ ID NO: 3)
iii. IADLVVGLCTGQIKTGAPCR (SEQ ID NO: 4)
iv. ADLVVGLCTGQIKTGAPCR (SEQ ID NO: 5)
v. DLVVGLCTGQIKTGAPCR (SEQ ID NO: 6)
vi. LVVGLCTGQIKTGAPCR (SEQ ID NO: 7)
vii. LVVGLCTGQIKTGPACR (SEQ ID NO: 8)
viii. LVVGLCTPQIKTGPACR (SEQ ID NO: 9)

By a preferred embodiment the invention provides a peptide capable of binding antibodies that are found in elevated levels in body fluids of schizophrenic patients selected from the group consisting of:
i. SGETEDTFIADLVVGLCTGQIKTGAPCR (SEQ ID NO: 2)
ii. LVVGLCTCQIKTGPAC (SEQ ID NO: 3)
iii. IADLVVGLCTGQIKTGAPCR (SEQ ID NO: 4)
iv. ADLVVGLCTGQIKTGAPCR (SEQ ID NO: 5)
v. DLVVGLCTGQIKTGAPCR (SEQ ID NO: 6)
vi. LVVGLCTGQIKTGAPCR (SEQ ID NO: 7)
vii. LVVGLCTGQIKTGPACR (SEQ ID NO: 8)
viii. LVVGLCTPQIKTGPACR (SEQ ID NO: 9)

The letters used above (and hereinafter) to denote specific a.a. are in accordance with the one-letter amino acid (a.a.) symbols recommended by the IUPAC-IUB Biochemical Nomenclature Commission.

Without being bound by theory, on the basis of the results obtained in accordance with the invention, it has become clear that the structure of the antigenic epitope of the peptides to which SDAs are capable of binding at a substantially higher decree as compared to NSDAs is a three-dimensional epitope. By using a computerized program based on minimal energy calculations, the antigenic epitope of a peptide in accordance with the invention is predicted as being a cyclic structure comprising a hydrophobic core and an extension having about two positive charges. The positive charged extensions may be positioned in one of many possible spatial orientations.

The binding activity of the peptide of the invention to various antibodies may be determined by any of the methods known per se such as ELISA or Western Blotting. For example, a tested peptide may be analyzed for its binding activity to antibodies by subjecting it to polyacrylamide gel electrophoresis, blotting it onto PVDS membranes which are then reacted with SDA and compared to their reaction with NSDA.

The extent of binding of the peptides of the invention to PAA can be determined by using any detection system known in the art such as antibodies against human immunoglobulin or fragments thereof linked to a detectable marker. The marker may be a radioactive group, a fluorescent group, an enzyme capable of catalyzing a reaction yielding a detectable product, a biotin group capable of being detected by avidin, etc.

By a preferred embodiment of this aspect, the peptides of the invention are bound onto a solid support such as e.g. a PVDF membrane, reacted with the tested sample and the level of binding of the PAAs in the sample is determined using an anti-human Fc antibody conjugated to a detectable marker.

In accordance with a particular embodiment, the determination of the level of autoantibodies bound to a tested peptide is determined by using anti-human Fc conjugated to horseradish peroxidase (SIGMA) and Fast-DAB™ (SIGMA) or 4-Chloro-naphthol (SIGMA) as the color reagent.

In order for the binding of the tested peptide in accordance with the invention to SDA to be considered "substantially higher" than its binding to NSDA, the level of binding to SDA should be statistically significantly higher than its binding to NSDA as determined by any of the statistical methods known in the art (e.g. Students' t-Test) which are used in connection with results obtained by the experimental methods mentioned above.

Analogs of all the above peptides also form an aspect of the present invention. As will be appreciated by any person versed in the art, the amino acid sequence of the peptides of the invention may be altered, for example by addition, replacement or deletion of one or more amino acids without substantially altering the binding capacity of the peptide to SDAs. Thus for example the leucine positioned in the first position of the amino acid to sequence of a peptide of the invention may be substituted by the amino acid glycine or valine which belong to the same family of amino acids without altering the binding activity of the peptide. A person versed in the art will have no difficulty in determining by which amino acid each of the amino acids of the peptide may be replaced in accordance with the known grouping of amino acids into families as may be found, for example, in Molecular Biology of the Cell Editors Alberts B. et al., Garland Publishing, Inc., New York and London, 2nd Edition, 1989, pages 54–55.

Analogs which fall under the scope of the peptides of the present invention are such which have substantially the same level of binding activity to SDAs, as the peptides i.e. have a higher level of binding to SDAs as compared to NSDAs as determined by any of the methods known in the art such as for example that described in Example 1 below.

The peptide of the invention may be obtained by enzymatic digestion (e.g. using Clostrapain) or chemical (CNBr) digestion of a longer protein. In such a case, the resulting peptides are separated by methods known in the art such as by RP-HPLC and the separate peptides may then be used for sequencing (e.g. by Eurosequence b.v. (Nijenborgh 4; 9749 Gronigen; The Netherlands)) and analyzed for their binding capability to SDAs as described above.

Peptides in accordance with the invention may also be synthesized by methods known in the art such as on Abimed 522 at a 10 µmol scale by Eurosequence b.v. (see detailed explanation in the examples below). The binding activity of the newly synthesized peptides will be determined using any of the assays mentioned above.

The peptides of the invention are capable of differentiating between a sample obtained from an individual suffering from schizophrenia and a sample obtained from a non-schizophrenic individual and are therefore useful in the diagnosis of schizophrenia in an individual. Thus, by another of its aspects, the present invention provides a peptide for use in the diagnosis of schizophrenia in an individual, said peptide capable of binding antibodies that are found in elevated levels in body fluids of schizophrenic patients.

The sample of the individual to be tested is typically a PAA containing fraction of a blood sample comprising platelets. However, in accordance with the present invention it has become possible for the first time to determine the probability of existence of schizophrenia in a plasma sample taken from tested individuals without the need to first isolate PAA from the sample. Thus, in accordance with the invention, the sample of an individual to be tested may either be a plasma sample or a PAA containing fraction obtained therefrom by any of the methods known in the art (e.g. by obtaining a platelet-rich plasma (PRP) and isolating PAA therefrom).

Since the peptides of the invention are capable of binding to a different extent to platelet derived autoantibodies in a sample obtained from a schizophrenic patient as compared to a sample obtained from a control non-schizophrenic individual, the peptides may be used in an assay for diagnosis of schizophrenia in an individual. Therefore, the present invention by an additional aspect provides an assay for the diagnosis of schizophrenia in an individual, comprising the following steps:
(a) obtaining a sample from said individual being a blood sample, a platelet-containing fraction thereof, or a fraction containing platelet-associated antibodies (PAA) shed from the platelets;
(b) contacting said sample with a peptide capable of binding to antibodies that are found in elevated levels in body fluids of schizophrenic patients.
(c) determining the level of binding of said peptide to said sample, a level higher than the binding level of said peptide to a sample from non-schizophrenic individuals indicating that said individual has a high likelihood of having schizophrenia.

By a further embodiment the peptide of step (b) above is a peptide which binds antibodies that are capable of specific binding to a peptide having the amino acid sequence of SEQ ID NO: 3. By another embodiment the peptide in step (b) above comprises an a. a. sequence selected from the group consisting of:
  i. SGETEDTFIADLVVGLCTGQIKTGAPCR (SEQ ID NO: 2)
  ii. LVVGLCTCQIKTGPAC (SEQ ID NO: 3)
  iii. IADLVVGLCTGQIKTGAPCR (SEQ ID NO: 4)
  iv. ADLVVGLCTGQIKTGAPCR (SEQ ID NO: 5)
  v. DLVVGLCTGQIKTGAPCR (SEQ ID NO: 6)
  vi. LVVGLCTGQIKTGAPCR (SEQ ID NO: 7)
  vii. LVVGLCTGQIKTGPACR (SEQ ID NO: 8)
  viii. LVVGLCTPQIKTGPACR (SEQ ID NO: 9)

By a preferred embodiment, the peptide in step (b) is a peptide selected from the group consisting of:
  i. SGETEDTFIADLVVGLCTGQIKTGAPCR (SEQ ID NO: 2)
  ii. LVVGLCTCQIKTGPAC (SEQ ID NO: 3)
  iii. IADLVVGLCTGQIKTGAPCR (SEQ ID NO: 4)
  iv. ADLVVGLCTGQIKTGAPCR (SEQ ID NO: 5)
  v. DLVVGLCTGQIKTGAPCR (SEQ ID NO: 6)
  vi. LVVGLCTGQIKTGAPCR (SEQ ID NO: 7)
  vii. LVVGLCTGQIKTGPACR (SEQ ID NO: 8)

The present invention also provides a kit useful in the above assay. The kit of the invention comprises a support comprising one or more peptides of the invention immobilized onto it and an anti-human immuno-globulin antibody or fragment thereof. The anti-HIG antibody may be conjugated to a detectable marker or alternatively, the kit may also comprise a second type of antibodies directed against said first antibodies, wherein the second antibodies are conjugated to a detectable marker. The kit will also comprise various reagents required for carrying out the assay as well as instructions for use.

The invention will now be illustrated in the following non-limiting description of specific embodiments and accompanying drawings.

Figure 1A:
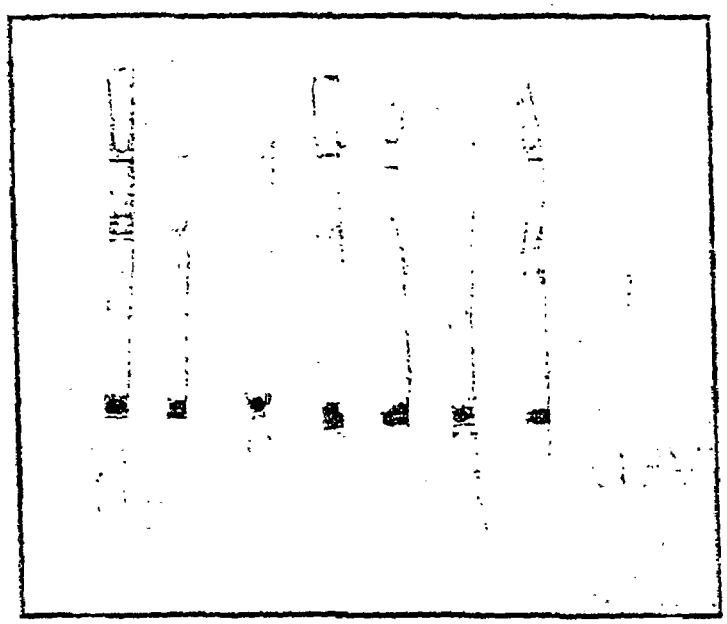
FIG. 1A is a graphical representation showing binding activity of the Peptide I4 having SEQ ID NO: 3 to PAAs prepared from samples obtained from schizophrenic patients. The peptide having SEQ ID NO: 10 was used as a negative control.

The amino acids found to exist in the epitope are marked as follows:

---

L = leucine
A = alanine
P = proline
R = arginine
K = hystidine

---

EXAMPLES

Materials and Methods

1. Platelets and Anti-Platelet Autoantibodies Venous blood (20 ml) was drawn with heparin as anticoagulant from patients and control subjects. Platelet rich plasma (PRP) was obtained by centrifugation (100 g for 20 mins) at room temperature. Plasma free platelets were obtained by washing them three times with phosphate buffered saline (PBS) supplemented with 10 ml mM EDTA as anticoagulant (4000 g; 15 mins; 4° C.). For the isolation of anti-platelet antibodies, the platelets were incubated with 0.1 M glycine/10 mM EDTA, pH 2.8, for 10 min. at room temperature and then centrifuged (4000 g; 15 min; 4° C.). The supernatant containing the anti-platelet antibodies, was neutralized with saturated $Na_2PO_4$ solution and stored at −20 until use.

2. Preparative Isoelectric Focusing

Platelet concentrates of blood group 0 were purchased from a local blood bank and washed three to five times with PBS/10 mM EDTA (4000 g; 15 min; 4° C.) until the supernatant was free of plasma. The platelets (about 20 concentrates) were first solubilized with 20 ml 0.5% Triton X-100/0.5% NP40 in water for 15 min. at room temperature under gentle shaking. The suspension was centrifuged (10000 g, 15 min. 4° C.), the supernatant removed and the pellet two more times extracted with 0.1% Triton X-110 in water. The three supernatants were combined and Ampholyte™ 3/10 (BioRad) was added to a final concentration of 1%. This solution was loaded into the ROTOFOR™ chamber (capacity 60 ml) and the preparative isoelectric focusing was then performed according to the instruction manual of the manufacturer (BioRad). Typically, the focusing was finished after 4.5 h (10° C.; 10 Watt constant power). Twenty fractions were harvested and the pH of the fractions determined (pH gradient 1.5~12). The fractions were stored at −20° C. until further use.

3. Identification of Immuno-Reactive Fractions

The fractions were analyzed for immuno-reactivity by polyacrylamide (10%) gel electrophoresis, blotting the proteins onto PVDF membranes and probing the membrane with 1 ml auto-antibodies in 50 ml incubation buffer. Anti-human Fc conjugated to horseradish peroxidase (goat) from SIGMA (1:500 dilution) and Fast-DAB™ (SIGMA) or 4-Chloro-naphthol (SIGMA) were used as color reagent in order to detect bound human anti-platelet antibodies. Immuno-reactivity was observed in the fractions with a pH ranging from 6.0 to 10.0.

4. Preparative Polyacrylamide (8%) Gel Electrophoresis

The immuno-reactive fractions (pH 6–10) were combined and separated according to molecular weight under reducing conditions by preparative SDS polyacrylamide gel (8% and 8 cm height) in a PrepCell from BioRad according to the instruction manual of the manufacturer. Fractions (n=400) of 1.5 ml were collected: every tenth fraction was analyzed by SDS gel electrophoresis followed by silver staining to determine the molecular weight distribution in the 400 fractions.

5. Identification of Immuno-Reactive Fractions

Every fifth fraction (0.1 ml) was dot blotted onto PVDF membranes using the DotBlot device (96 wells) from Bio-Rad. Immuno-reactive fractions were then detected as described above (1.3)

6. Identification of Immuno-Reactive Proteins

As described previously, a variety of immuno-reactive proteins were identified. Priority for sequencing was given to proteins with a high ratio of reactivity to protein amount. Preparation of sample was typically done in the following way: The fractions (+/− 10) around a positive fraction were re-analyzed as described above under 1.5. The positive fractions were combined, lyophilized, re-separated on an analytical (0.75 mm) SDS polyacrylamide (10%) gel and stained with Coomassie Blue. The band was excised and sent to Eurosequence b.v. (enzymatic digestion, RP-HPLC separation of peptides followed by acid sequencing).

7. Identification of Immuno-Reactive Epitope

Of the identified proteins, two were found to be commercially available:
a) Glyceraldehyde-6-phosphate dehydrogenase (G6PD)
b) Enolase About 10 mg protein was digested either enzymatically (Clostrapain) or chemically (CNBr) and the resulting peptides were separated by RP-HPLC Aliquot (20%) of all fractions were sent by Eurosequence b.v. to the Main Inventor for analysis of immuno-reactivity as described under 1.5. Only the enzymatic digest of the Enolase resulted in an active fragment which was subsequently sequenced by Eurosequence b.v.

8. Peptide Synthesis

Various peptides were synthesized on Abimed 522 at a 10 micromol scale by Eurosequence b.v. Peptides were routinely dissolved in 1 ml water/DMF/DMSO (1:1:1;v/v/v). Peptides were line-blotted onto PVDF membranes and tested for immuno-reactivity as described above.

9. Epitope Scanning

Water models of the peptides of the invention were calculated on a MacIntosh computer system. An x-ray three dimensional structure of enolase was generated from a public peptide database and the surface of the enolase was scanned to find epitopes which match the epitopes of the peptides calculated by the water model.

Example 1

Identification of Immuno-Reactive Proteins

The following proteins have been identified as such capable of binding autoantibodies present in high levels in schizophrenic patients at a high level as determined by the assay described in 1.3 above:

Protein:
Glyceraldehyde-6-phosphate dehydrogenase
Enolase
Keratin
Hepatocyte growth factor
Extracellular calcium sensing receptor The above identified proteins were tested for their binding capability to plasma samples obtained from schizophrenic patients and to plasma samples obtained from control non-schizophrenic patients. The results showed that it was not possible to use the above proteins to discriminate between a plasma sample obtained from a schizophrenic patient and that obtained from a non-schizophrenic individual. i.e. the binding results were not conclusive.

The binding activity of the above two enzymes was then tested by reacting them with SDAs (prepared from samples obtained from schizophrenic patients) and to NSDA (prepared from control non-schizophrenic individuals). As seen in Table 1 below, in this case binding of the proteins to SDAs was substantially higher than their binding to NSDAs expressed by the number of samples that reacted positively with each of the enzymes.

TABLE 1

| Reactivity of proteins to SDAs and NSDAs | | |
|---|---|---|
| Enzyme | Patients (n = 8) Positive | Controls (n = 8) Positive |
| G-3-P-Dehydrogenase | | |
| from human | 7/8 | 1/8 |
| from pig | 8/8 | 1/8 |
| from chicken | 7/8 | 2/8 |

TABLE 1-continued

Reactivity of proteins to SDAs and NSDAs

| Enzyme | Patients (n = 8) Positive | Controls (n = 8) Positive |
| --- | --- | --- |
| from yeast | 6/8 | 1/8 |
| from *bacillus subtilis* | 1/8 | 2/8 |
| Enolase | | |
| from Rabbit | 7/8 | 1/8 |

The above results showed that the proteins obtained in accordance with the invention may be useful in the diagnosis of schizophrenia in a tested individual but require that the sample obtained and tested from the individual will comprise of prepared platelet-derived autoantibodies. The enzymes are not suitable for detecting, schizophrenia directly in a plasma sample.

Example 2

Identification of the Epitope in the Digested Proteins Capable of Specific Binding to SDAs:

Only the enzymatic digest of the Enolase revealed one peptide which was immunologically active (amino acids 372–399; The peptide having SEQ ID NO: 2 in the following Table 2), i.e. was capable of binding SDAs to a higher extent and its capability of binding to NSDAs.

Based on the sequence of the epitope identified in the digested proteins, a number of peptides were synthesized by the method described in 1.8 above. The synthesized peptides were then evaluated for their binding activity to SDAs as compared to NSDAs as described above.

As seen in Table 2 below, several of the synthesized peptides showed a substantially higher binding activity to SDAs as compared to their binding to NSDAs (indicated as YES in the table) while others showed no significant differences in their binding to samples from schizophrenic and non-schizophrenic individuals (designed as no in the table).

TABLE 2

| Peptide | | Seq. I.D. No. | Activity |
| --- | --- | --- | --- |
| SGETEDTFIADLVVGLCTGQIKTGAPCR | (28aa) | 2 | YES |
| LVVGLCTCQUKTGPAC | (17aa) | 3 | YES |
| IADLVVGLCTGQIKTGAPCR | (20aa) | 4 | YES |
| ADLVVGLCTGQIKTGAPCR | (19aa) | 5 | YES |
| DLVVGLCTGQIKTGAPCR | (18aa) | 6 | YES |
| LVVGLCTGQIKTGAPCR | (17aa) | 7 | YES |
| LVVGLCTGQUKTGPACR | (17aa) | 8 | YES |
| LVVGLCTPQUKTGPACR | (17aa) | 9 | YES |
| SGETEDTFIADLVVGLCTGQ | (20aa) | 10 | No |
| WGLCTGQIKTGAPCR | (16aa) | 11 | No |
| CTGQIKTGAPCR | (12aa) | 12 | No |
| LVVGLCTGQIKTGAPC | (16aa) | 13 | No |
| LVVGLCTGQIKTGAP | (15aa) | 14 | No |
| LVVGLCTGQIKTGPAC | (16aa) | 15 | No |

Of the synthesized peptides, Peptide SEQ ID NO: 3 was most capable of binding to antibodies found in high levels in schizophrenic patients.

Example 3

Characterization of Peptide SEQ ID NO: 3

Laser desorption mass spectroscopy of Peptide SEQ ID NO: 3 (comprising three cysteins) directly after synthesis shows the presence of a monomer without a ring formation via the cysteins. However, after dissolving the peptide (about 4 mg) in 1 ml water/DMF/DMSO (1:1:1;v:v:v) and leaving the solution overnight at room temperature, the peptide forms a ring via two cysteins and a dimer via the remaining free cystein. No higher polymers could be detected. When testing the binding activity of the two forms of the peptide to SDA, it became clear that the dimer form of the peptide was much more active in binding SDAs than the non-dimer form.

Chemical analysis of the peptide by reduction, e.g. by mercaptoethanol or sodium borohydrid, destroyed the immunological activity completely, whereas oxidation, e.g. air or oxygen, restored the immunological activity.

Example 4

Figure 1B:
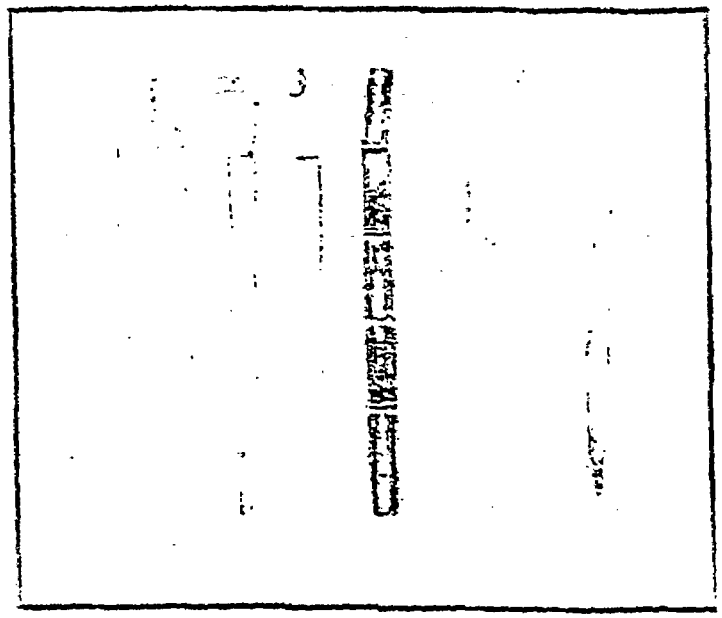
FIG. 1B is a graphical representation showing binding activity of the Peptide I4 having SEQ ID NO: 3 to PAAs prepared from samples obtained from non-schizophrenic individuals. The peptide having SEQ ID NO: 10 was used as a negative control.

Binding activity of Peptide SEQ ID NO: 3 to Samples from Schizophrenic and non-schizophrenic Individuals The binding activity of Peptide 14 (SEQ ID NO: 3) to isolated PAAs was tested using the method described above. As seen in FIG. 1A, the above peptide positively bound seven out of eight PAAs obtained from different schizophrenic patients. FIG. 1B shows that the above peptide did not bind PAAs obtained from eight different non-schizophrenic individuals. Peptide SEQ ID NO: 10 was used as a negative control.

Figure 2A:
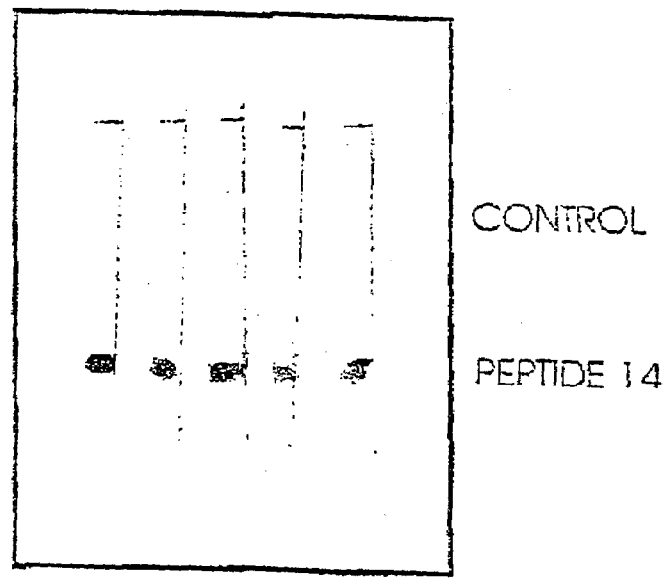
FIG. 2A is a graphical representation showing binding activity of peptide I4 (SEQ ID NO: 3) to plasma samples obtained from schizophrenic patients. The peptide having SEQ ID NO: 10 was used as a negative control.
Figure 2B:
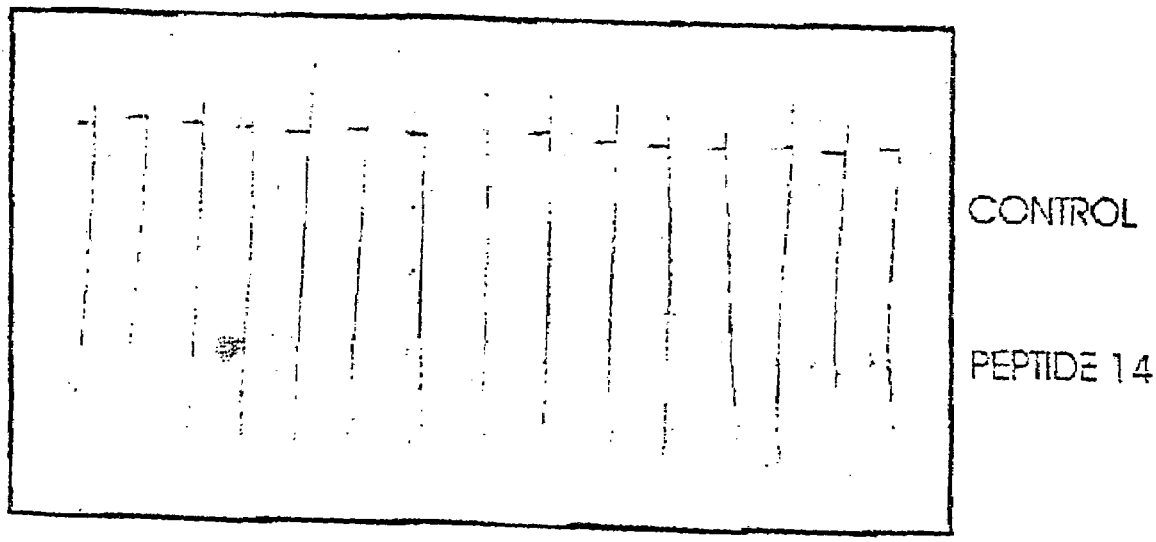
FIG. 2B is a graphical representation showing binding activity of peptide I4 (SEQ ID NO: 3) to plasma samples obtained from non-schizophrenic individuals. The peptide having SEQ ID NO: 10 was used as a negative control.

The capability of Peptide 14 (SEQ ID NO: 3) to bind SDA in plasma samples obtained from schizophrenic patients was then tested. As seen in FIG. 2A, this peptide positively bound four out of five SDA from different schizophrenic patients. FIG. 2B shows that the above peptide did not bind NSDA from fourteen out of fifteen different non-schizophrenic individuals. Peptide 14 (SEQ ID NO: 10) was used as a negative control.

Example 5

Three Dimensional Structure:

The three-dimensional structure of the antigenic epitope of peptides according to the invention was predicted using a computerized program based on the mineral energy calculations.

Figure 3:
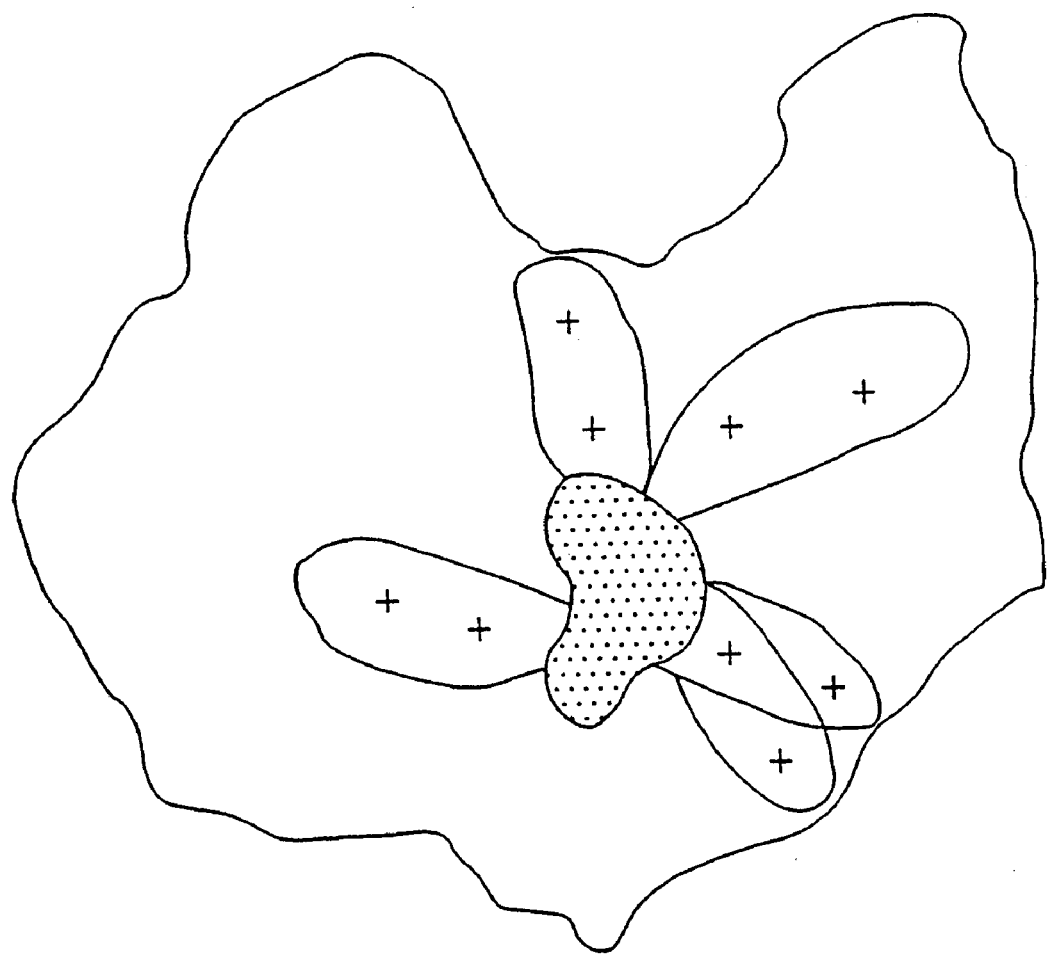
FIG. 3 is a graphical representation showing a schematically predicted three-dimensional structure of the antigenic epitope of the peptides of the invention as determined by a computerized program based on minimal energy calculations.

As seen in FIG. 3, the predicted structure of the antigenic epitope is a cyclic structure comprising a hydrophobic core and an extension comprising about two positive charges. The positive charged extensions may be positioned in one of many possible spatial orientations.

Example 6

Scanning of the Surface of the Enolase to find Epitopes Matching the Calculated Epitopes of the Peptides The water model three-dimensional structure of the peptides of the invention was calculated. An x-ray three-dimensional structure of enolase generated from a public peptide database was then scanned and the position of the amino acids of the peptides of the invention was compared to the position of the amino acids of the enolase surface to see if an epitope which matches one or more of the calculated epitopes of the peptides of the invention could be found on the surface of the enolase.

Figure 4:
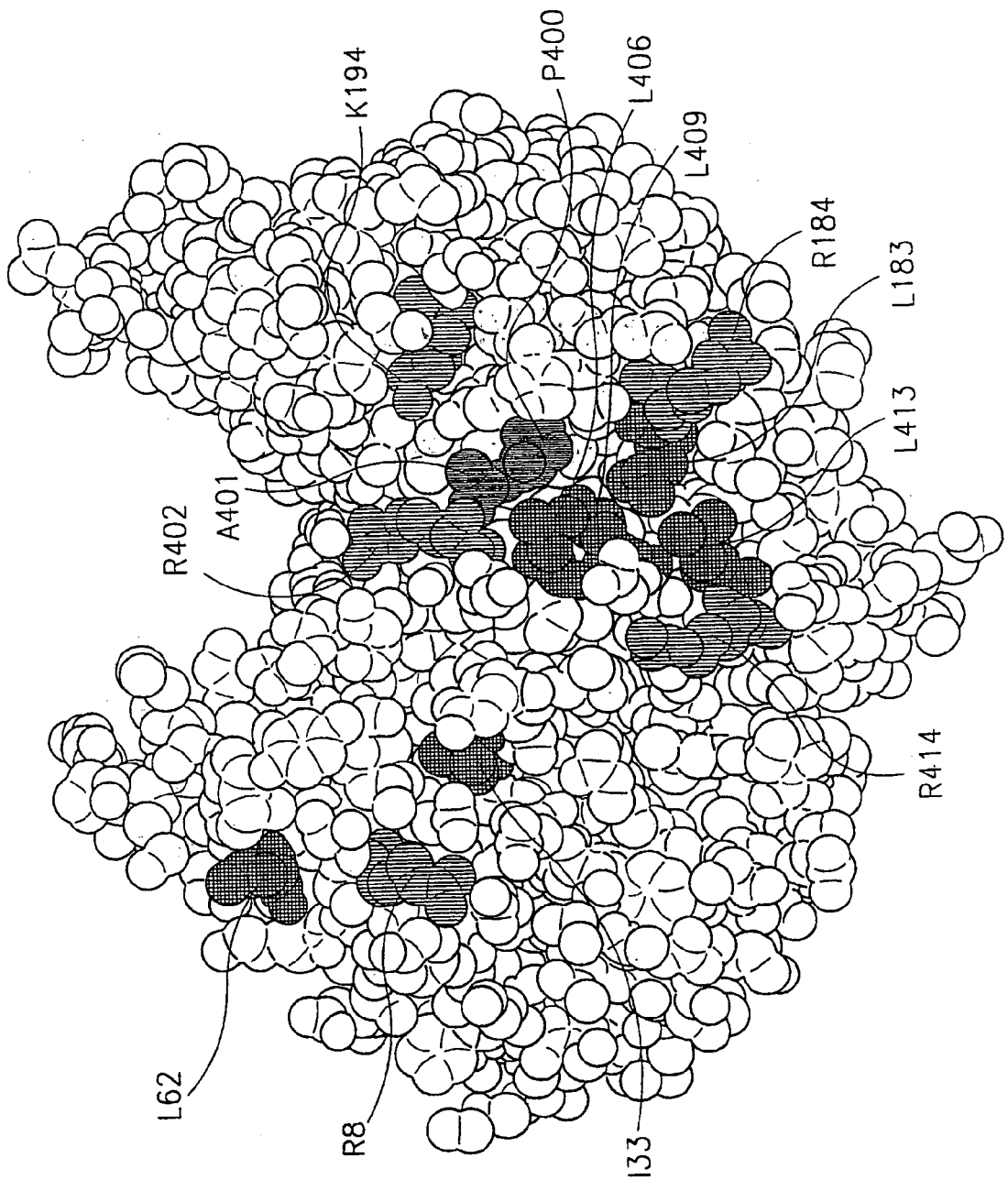
FIG. 4 is an x-ray of a three-dimensional structure of enolase generated from a public peptide database and compared with the water model of the peptides of the invention.

As seen in FIG. 4 which is a computer simulation of the scanning of the surface of the enolase, an epitope was found on the surface of the enolase which is comprised of a cluster of hydrophobic amino acids (Leucine, Alanine and Proline) surrounded by positive charged amino acids (Arginine and Hystidine) which matches the epitope simulated from the peptides of the invention. Thus, the predicted structure of the antigenic epitope of the peptides of the invention could indeed be found on the cell surface of enolase.

What is claimed is:

1. An isolated peptide, comprising SEQ ID NO: 3.
2. A composition, comprising the isolated peptide of claim 1, and a carrier.

\* \* \* \* \*

SEQUENCE LISTING

```
<160> NUMBER OF SEQ ID NOS: 15

<210> SEQ ID NO 1
<211> LENGTH: 28
<212> TYPE: PRT
<213> ORGANISM: Artificial Sequence
<220> FEATURE:
<223> OTHER INFORMATION: being the immunologically active epitope
<220> FEATURE:
<221> NAME/KEY: MISC_FEATURE
<222> LOCATION: (1)..(1)
<223> OTHER INFORMATION: Xaa(1) is S or absent
<220> FEATURE:
<221> NAME/KEY: MISC_FEATURE
<222> LOCATION: (1)..(11)
<223> OTHER INFORMATION: provided that when Xaa(11) is absent, Xaa(1)
      through Xaa(10), inclusive, are absent, and when Xaa(11) is D,
      Xaa(10) is A or absent
<220> FEATURE:
<221> NAME/KEY: MISC_FEATURE
<222> LOCATION: (1)..(10)
<223> OTHER INFORMATION: when Xaa(10) is absent, Xaa(1) through Xaa(9),
      inclusive, are absent, and when Xaa(10) is A, Xaa(9) is I or
      absent
<220> FEATURE:
<221> NAME/KEY: MISC_FEATURE
<222> LOCATION: (1)..(9)
<223> OTHER INFORMATION: when Xaa(9) is absent, Xaa(1) through Xaa(8),
      inclusive, are absent, and when Xaa(9) is I, Xaa(8) is F or absent
<220> FEATURE:
<221> NAME/KEY: MISC_FEATURE
<222> LOCATION: (1)..(8)
<223> OTHER INFORMATION: when Xaa(8) is absent, Xaa(1) through Xaa(7),
      inclusive, are absent, and when Xaa(8) is F, Xaa(1) through Xaa(7)
      are, respectively, S, G, E, T, E, D, and T
<220> FEATURE:
<221> NAME/KEY: MISC_FEATURE
<222> LOCATION: (2)..(2)
<223> OTHER INFORMATION: Xaa(2) is G or absent
<220> FEATURE:
<221> NAME/KEY: MISC_FEATURE
<222> LOCATION: (3)..(3)
<223> OTHER INFORMATION: Xaa(3) is E or absent
<220> FEATURE:
<221> NAME/KEY: MISC_FEATURE
<222> LOCATION: (4)..(4)
<223> OTHER INFORMATION: Xaa(4) is T or absent
<220> FEATURE:
<221> NAME/KEY: MISC_FEATURE
<222> LOCATION: (5)..(5)
<223> OTHER INFORMATION: Xaa(5) is E or absent
<220> FEATURE:
<221> NAME/KEY: MISC_FEATURE
<222> LOCATION: (6)..(6)
<223> OTHER INFORMATION: Xaa(6) is D or absent
<220> FEATURE:
<221> NAME/KEY: MISC_FEATURE
<222> LOCATION: (7)..(7)
<223> OTHER INFORMATION: Xaa(7) is T or absent
<220> FEATURE:
<221> NAME/KEY: MISC_FEATURE
<222> LOCATION: (8)..(8)
<223> OTHER INFORMATION: Xaa(8) is F or absent
<220> FEATURE:
<221> NAME/KEY: MISC_FEATURE
```

```
<222> LOCATION: (9)..(9)
<223> OTHER INFORMATION: Xaa(9) is I or absent
<220> FEATURE:
<221> NAME/KEY: MISC_FEATURE
<222> LOCATION: (10)..(10)
<223> OTHER INFORMATION: Xaa(10) is A or absent
<220> FEATURE:
<221> NAME/KEY: MISC_FEATURE
<222> LOCATION: (19)..(19)
<223> OTHER INFORMATION: Xaa(19) is C, G, P
<220> FEATURE:
<221> NAME/KEY: MISC_FEATURE
<222> LOCATION: (25)..(25)
<223> OTHER INFORMATION: Xaa(25) is A, P
<220> FEATURE:
<221> NAME/KEY: MISC_FEATURE
<222> LOCATION: (25)..(28)
<223> OTHER INFORMATION: Xaa(28) is R or absent, provided that Xaa(25)
      and Xaa(26) are taken together to form a sequence selected from
      the group consisting of AP and PA
<220> FEATURE:
<221> NAME/KEY: MISC_FEATURE
<222> LOCATION: (26)..(26)
<223> OTHER INFORMATION: Xaa(26) is P, A

<400> SEQUENCE: 1

Xaa Xaa Xaa Xaa Xaa Xaa Xaa Xaa Xaa Xaa Xaa Leu Val Val Gly Leu
1               5                   10                  15

Cys Thr Xaa Gln Ile Lys Thr Gly Xaa Xaa Cys Xaa
            20                  25

<210> SEQ ID NO 2
<211> LENGTH: 28
<212> TYPE: PRT
<213> ORGANISM: Artificial Sequence
<220> FEATURE:
<223> OTHER INFORMATION: being the immunologically active epitope

<400> SEQUENCE: 2

Ser Gly Glu Thr Glu Asp Thr Phe Ile Ala Asp Leu Val Val Gly Leu
1               5                   10                  15

Cys Thr Gly Gln Ile Lys Thr Gly Ala Pro Cys Arg
            20                  25

<210> SEQ ID NO 3
<211> LENGTH: 16
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 3

Leu Val Val Gly Leu Cys Thr Cys Gln Ile Lys Thr Gly Pro Ala Cys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 4

Ile Ala Asp Leu Val Val Gly Leu Cys Thr Gly Gln Ile Lys Thr Gly
1               5                   10                  15

Ala Pro Cys Arg
            20
```

```
<210> SEQ ID NO 5
<211> LENGTH: 19
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 5

Ala Asp Leu Val Val Gly Leu Cys Thr Gly Gln Ile Lys Thr Gly Ala
1               5                   10                  15

Pro Cys Arg

<210> SEQ ID NO 6
<211> LENGTH: 18
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 6

Asp Leu Val Val Gly Leu Cys Thr Gly Gln Ile Lys Thr Gly Ala Pro
1               5                   10                  15

Cys Arg

<210> SEQ ID NO 7
<211> LENGTH: 17
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 7

Leu Val Val Gly Leu Cys Thr Gly Gln Ile Lys Thr Gly Ala Pro Cys
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 8

Leu Val Val Gly Leu Cys Thr Gly Gln Ile Lys Thr Gly Pro Ala Cys
1               5                   10                  15

Arg

<210> SEQ ID NO 9
<211> LENGTH: 17
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 9

Leu Val Val Gly Leu Cys Thr Pro Gln Ile Lys Thr Gly Pro Ala Cys
1               5                   10                  15
```

-continued

Arg

<210> SEQ ID NO 10
<211> LENGTH: 20
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 10

Ser Gly Glu Thr Glu Asp Thr Phe Ile Ala Asp Leu Val Val Gly Leu
1               5                   10                  15

Cys Thr Gly Gln
            20

<210> SEQ ID NO 11
<211> LENGTH: 16
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 11

Val Val Gly Leu Cys Thr Gly Gln Ile Lys Thr Gly Ala Pro Cys Arg
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 12

Cys Thr Gly Gln Ile Lys Thr Gly Ala Pro Cys Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 13

Leu Val Val Gly Leu Cys Thr Gly Gln Ile Lys Thr Gly Ala Pro Cys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 14

Leu Val Val Gly Leu Cys Thr Gly Gln Ile Lys Thr Gly Ala Pro
1               5                   10                  15

<210> SEQ ID NO 15
<211> LENGTH: 16
<212> TYPE: PRT

-continued

```
<213> ORGANISM: Artificial Sequence
<220> FEATURE:
<223> OTHER INFORMATION: peptide capable of binding antibodies that are
      found in elevated levels in body fluids of schizophrenic patients.

<400> SEQUENCE: 15

Leu Val Val Gly Leu Cys Thr Gly Gln Ile Lys Thr Gly Pro Ala Cys
1               5                   10                  15
```